United States Patent
Rouge et al.

(10) Patent No.: US 11,786,276 B2
(45) Date of Patent: *Oct. 17, 2023

(54) DEVICES AND METHODS FOR BENDING OR CUTTING IMPLANTS

(71) Applicant: Medos International Sarl, Le Locle (CH)

(72) Inventors: Renaud Rouge, Le Locle (CH); Jakub Galkowski, Le Locle (CH); Thibault Chandanson, Villers le lac (FR)

(73) Assignee: Medos International Sarl, Le Locle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/855,718

(22) Filed: Jun. 30, 2022

(65) Prior Publication Data

US 2022/0330990 A1    Oct. 20, 2022

Related U.S. Application Data

(60) Continuation of application No. 16/266,849, filed on Feb. 4, 2019, now Pat. No. 11,399,876, which is a
(Continued)

(51) Int. Cl.
*A61B 17/70* (2006.01)
*B21D 7/024* (2006.01)

(52) U.S. Cl.
CPC ...... *A61B 17/7074* (2013.01); *A61B 17/7013* (2013.01); *B21D 7/024* (2013.01)

(58) Field of Classification Search
CPC .. B21D 7/00; B21D 7/02; B21D 7/024; A61B 17/7074; A61B 17/7013
See application file for complete search history.

(56) References Cited

U.S. PATENT DOCUMENTS

| 401,308 A | 4/1889 | Selleck |
| 1,636,786 A | 7/1927 | Rolley |

(Continued)

FOREIGN PATENT DOCUMENTS

| GB | 461399 A | 2/1937 |
| WO | 2014088801 A1 | 6/2014 |
| WO | 2014143762 A2 | 9/2014 |

OTHER PUBLICATIONS

[No Author Listed] Expedium® 5.5 Titanium Spine System, Product Catalog; 2013 DePuy Synthes Spine (34 pages).

*Primary Examiner* — Teresa M Ekiert
(74) *Attorney, Agent, or Firm* — Barnes & Thornburg LLP

(57) ABSTRACT

Devices and methods for bending or cutting implants are disclosed herein. In some embodiments, an instrument can convert a rotational input force (e.g., supplied by a powered driver tool) into movement of a first rod holder with respect to a second rod holder. Such movement can form a bend in a rod or other implant held by the first and second rod holders. Various mechanisms for converting this movement are disclosed, such as a worm drive mechanism and a conical gear mechanism, as are various types of rod holders, including orbiting rollers, lid-type rod holders, fixed and pivoting half-pipe rod holders, and full-pipe rod holders. In some embodiments, the instrument can also be used for cutting, for example by rotating a cutting wheel with respect to a cutting plate to cut a rod or other implant inserted through openings formed in the cutting wheel and the cutting plate.

31 Claims, 13 Drawing Sheets

Related U.S. Application Data division of application No. 15/154,717, filed on May 13, 2016, now Pat. No. 10,194,957.

(56) References Cited

U.S. PATENT DOCUMENTS

| | | | |
|---|---|---|---|
| 1,775,761 | A | 9/1930 | Harvey et al. |
| 2,762,415 | A | 9/1956 | Franck |
| 2,818,786 | A | 1/1958 | Hammer |
| 2,986,195 | A | 5/1961 | Landis |
| 3,260,091 | A | 7/1966 | Shaw, Jr. |
| 3,575,032 | A | 4/1971 | Zahuranec et al. |
| 3,680,347 | A | 8/1972 | Schenck et al. |
| 4,888,971 | A | 12/1989 | Schwarze |
| 5,144,829 | A | 9/1992 | Fabro et al. |
| 5,243,760 | A | 9/1993 | May, Jr. |
| 6,644,087 | B1 | 11/2003 | Ralph et al. |
| 6,755,064 | B2 | 6/2004 | Butscher et al. |
| 7,882,721 | B2 | 2/2011 | Gombas |
| 8,177,843 | B2 | 5/2012 | Schalliol |
| 8,235,998 | B2 | 8/2012 | Miller et al. |
| 8,266,940 | B2 | 9/2012 | Riemeier et al. |
| 8,298,242 | B2 | 10/2012 | Justis et al. |
| 8,333,097 | B1 | 12/2012 | Frear |
| 8,607,603 | B2 | 12/2013 | Justis et al. |
| 8,935,974 | B2 | 1/2015 | Crainich et al. |
| 8,991,229 | B1 * | 3/2015 | Cheng ............... B21D 7/024 72/149 |
| 10,070,909 | B2 | 9/2018 | Rouge et al. |
| 10,076,376 | B2 | 9/2018 | Bootwala et al. |
| 10,194,957 | B2 | 2/2019 | Rouge et al. |
| 11,033,314 | B2 | 6/2021 | Rouge et al. |
| 2003/0055435 | A1 | 3/2003 | Barrick |
| 2004/0144149 | A1 | 7/2004 | Strippgen et al. |
| 2005/0262911 | A1 | 12/2005 | Dankowicz et al. |
| 2006/0037198 | A1 | 2/2006 | Sullivan |
| 2010/0111631 | A1 | 5/2010 | Trieu et al. |
| 2012/0186411 | A1 | 7/2012 | Lodahi et al. |
| 2012/0247173 | A1 * | 10/2012 | Paris ............... B21D 7/063 72/458 |
| 2014/0000335 | A1 | 1/2014 | Fries et al. |
| 2014/0066994 | A1 | 3/2014 | Dominik et al. |
| 2014/0311203 | A1 | 10/2014 | Crawford et al. |
| 2016/0074918 | A1 * | 3/2016 | Latoria ............... B21D 7/063 72/219 |
| 2016/0082493 | A1 | 3/2016 | Neal et al. |
| 2016/0089195 | A1 * | 3/2016 | Cordaro ........... A61B 17/7085 606/279 |
| 2016/0346026 | A1 | 12/2016 | Bootwala et al. |
| 2016/0346027 | A1 | 12/2016 | Rouge et al. |
| 2017/0325854 | A1 | 11/2017 | Rouge et al. |
| 2019/0038332 | A1 | 2/2019 | Rouge et al. |
| 2019/0167317 | A1 | 6/2019 | Rouge et al. |
| 2021/0275239 | A1 | 9/2021 | Rouge et al. |

* cited by examiner

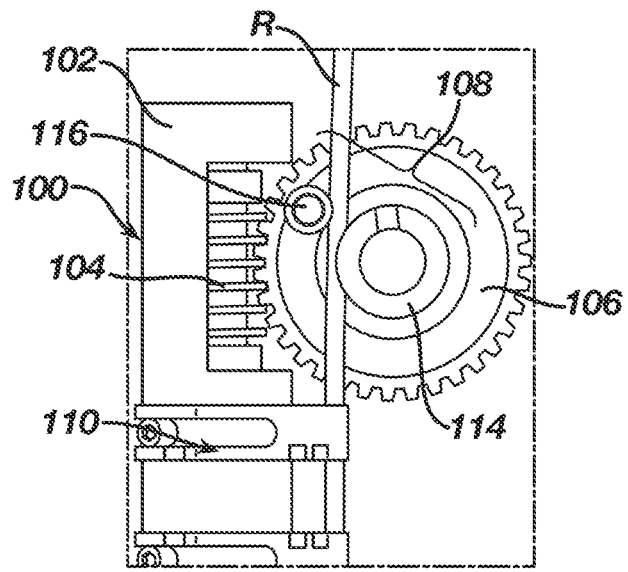
FIG. 1N
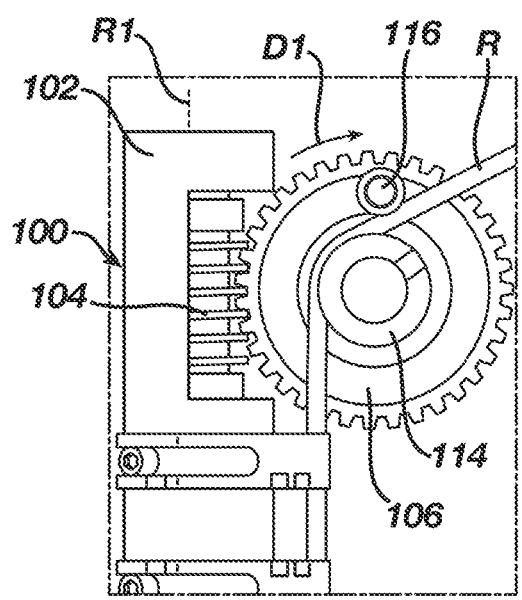 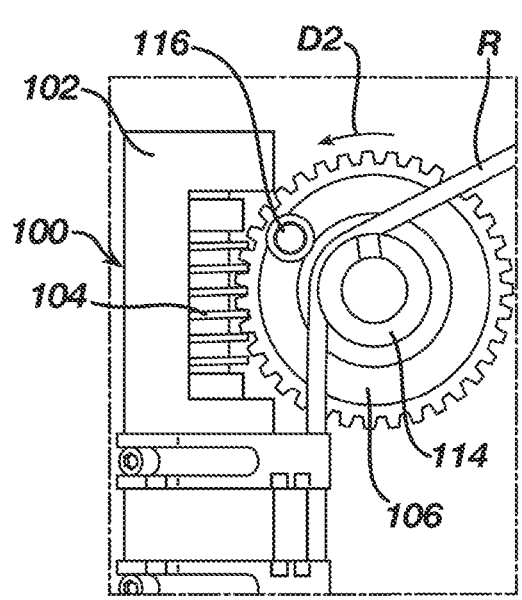
FIG. 1O  FIG. 1P

DEVICES AND METHODS FOR BENDING OR CUTTING IMPLANTS

CROSS-REFERENCE TO RELATED APPLICATIONS

This application is a continuation of U.S. application Ser. No. 16/266,849, filed Feb. 4, 2019, entitled "Devices and Methods for Bending or Cutting Implants." U.S. application Ser. No. 16/266,849 is a divisional of U.S. application Ser. No. 15/154,717, filed May 13, 2016, entitled "Devices and Methods for Bending or Cutting Implants," now issued as U.S. Pat. No. 10,194,957. Each of these applications is hereby incorporated by reference in its entirety.

FIELD

Devices and methods for bending or cutting implants are disclosed herein.

BACKGROUND

There is often a need to bend or cut an implant during a surgical procedure or in preparation for a surgical procedure. For example, spinal rods are typically cut to a desired length and bent to a desired shape before being implanted in a patient. Often times, several bends are necessary to form a compound or complex bend along the length of a large rod. Forming the final shape can be an iterative process in which the rod is bent, checked for fit, and then bent again until the desired shape is achieved.

Existing solutions for bending or cutting rods have numerous shortcomings. The bending and cutting tools used today are very large and are not capable of bending a rod that is at least partially implanted in the patient. Instead, these tools are typically used at a back table in the operating room, remote from the patient and the surgical site. As a result, the surgeon usually needs to make several trips back and forth between the patient and the back table to make adjustments until the final rod shape is achieved. Existing tools also require significant input force from the surgeon, which increases surgeon fatigue. These tools also lack precision, which increases the number of adjustments that must be made to the rod. In some cases, repeated bending and adjustment of the rod can reduce the rod strength.

There is a continual need for improved bending and/or cutting devices and related methods.

SUMMARY

Devices and methods for bending or cutting implants are disclosed herein. In some embodiments, an instrument can convert a rotational input force (e.g., supplied by a powered driver tool) into movement of a first rod holder with respect to a second rod holder. Such movement can form a bend in a rod or other implant held by the first and second rod holders. Various mechanisms for converting this movement are disclosed, such as a worm drive mechanism and a conical gear mechanism, as are various types of rod holders, including orbiting rollers, lid-type rod holders, fixed and pivoting half-pipe rod holders, and full-pipe rod holders. In some embodiments, the instrument can also be used for cutting, for example by rotating a cutting wheel with respect to a cutting plate to cut a rod or other implant inserted through openings formed in the cutting wheel and the cutting plate.

In some embodiments, an instrument for bending an implant includes a chassis having a drive shaft disposed therein, the drive shaft being configured to rotate a gear rotatably mounted to the chassis; a first rod holder mounted on the gear and configured to receive a portion of an implant therein; and a second rod holder mounted on the chassis and configured to receive a portion of an implant therein; wherein rotation of the gear causes the first rod holder to move relative to the second rod holder to form a bend in an implant received in the first and second rod holders.

The drive shaft can rotate about a first axis and the gear can rotate about a second axis, the second axis being perpendicular to a plane in which the first axis lies. The gear can include a worm gear and the drive shaft can include a worm screw configured to rotate the worm gear when the drive shaft rotates. The gear can include a first conical gear and the drive shaft can include a second conical gear enmeshed with the first conical gear. The first rod holder can include a main roller and a secondary roller configured to orbit the main roller when the gear rotates. At least one of the main roller and the secondary roller can include an annular groove formed therein for receiving an implant. At least one of the main roller and the secondary roller can include a plurality of arcuate portions, each arcuate portion having a different radius of curvature. The instrument can include a cutting plate having an implant opening formed therein. The main roller can include an implant opening formed therein. Rotation of the main roller relative to the cutting plate can be effective to cut an implant extending through the implant openings of the main roller and the cutting plate. The first rod holder can include a half-pipe fixedly mounted to the gear. The first rod holder can include a half-pipe rotatably mounted to the gear. The second rod holder can include first and second mounts with a lid pivotally attached thereto. The first and second mounts can include respective rod seats. The lid can have an open position in which an implant can be freely moved with respect to the rod seats and a closed position in which the lid holds the implant in contact with the rod seats. The lid can include opposed pivot pegs that slide within respective slots formed in the first and second mounts. The lid can include opposed locking pegs that are received within respective first recesses of the first and second mounts when the lid is in the open position and that are received within respective second recesses of the first and second mounts when the lid is in the closed position.

In some embodiments, a method of bending an implant using a bending instrument having a drive shaft, a gear, and first and second rod holders, includes positioning the implant such that it is received in the first and second rod holders; and rotating the drive shaft to cause the gear to rotate; wherein rotation of the gear causes the first rod holder to move relative to the second rod holder to form a bend in the implant.

The first rod holder can include a main roller and a secondary roller. Rotating the gear can cause the secondary roller to orbit the main roller to bend the implant disposed therebetween. The method can include selecting one of a plurality of arcuate portions of the main roller and positioning the selected arcuate portion in contact with the implant before bending the implant. The method can include cutting the implant by inserting the implant through a first opening formed in an axle portion of the gear and a second opening formed in a cutting plate of the instrument and then rotating the gear relative to the cutting plate. Positioning the implant in the second rod holder can include closing a lid of the second rod holder over the implant to lock the implant to first and second seat portions of the second rod holder. The first rod holder can include a half-pipe. Rotating the gear can cause the half-pipe to pivot relative to the gear as the implant is bent.

BRIEF DESCRIPTION OF THE DRAWINGS

The following detailed description is provided with the accompanying drawings, in which:

FIG. 1N is a perspective view of the instrument of FIG. 1A having a rod disposed therein prior to actuation;

FIG. 1O is a perspective view of the instrument of FIG. 1A bending a rod disposed therein;

FIG. 1P is a perspective view of the instrument of FIG. 1A having a bent rod disposed therein after retraction of a secondary roller;

DETAILED DESCRIPTION

Devices and methods for bending or cutting implants are disclosed herein. In some embodiments, an instrument can convert a rotational input force (e.g., supplied by a powered driver tool) into movement of a first rod holder with respect to a second rod holder. Such movement can form a bend in a rod or other implant held by the first and second rod holders. Various mechanisms for converting this movement are disclosed, such as a worm drive mechanism and a conical gear mechanism, as are various types of rod holders, including orbiting rollers, lid-type rod holders, fixed and pivoting half-pipe rod holders, and full-pipe rod holders. In some embodiments, the instrument can also be used for cutting, for example by rotating a cutting wheel with respect to a cutting plate to cut a rod or other implant inserted through openings formed in the cutting wheel and the cutting plate.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Figure 1A:
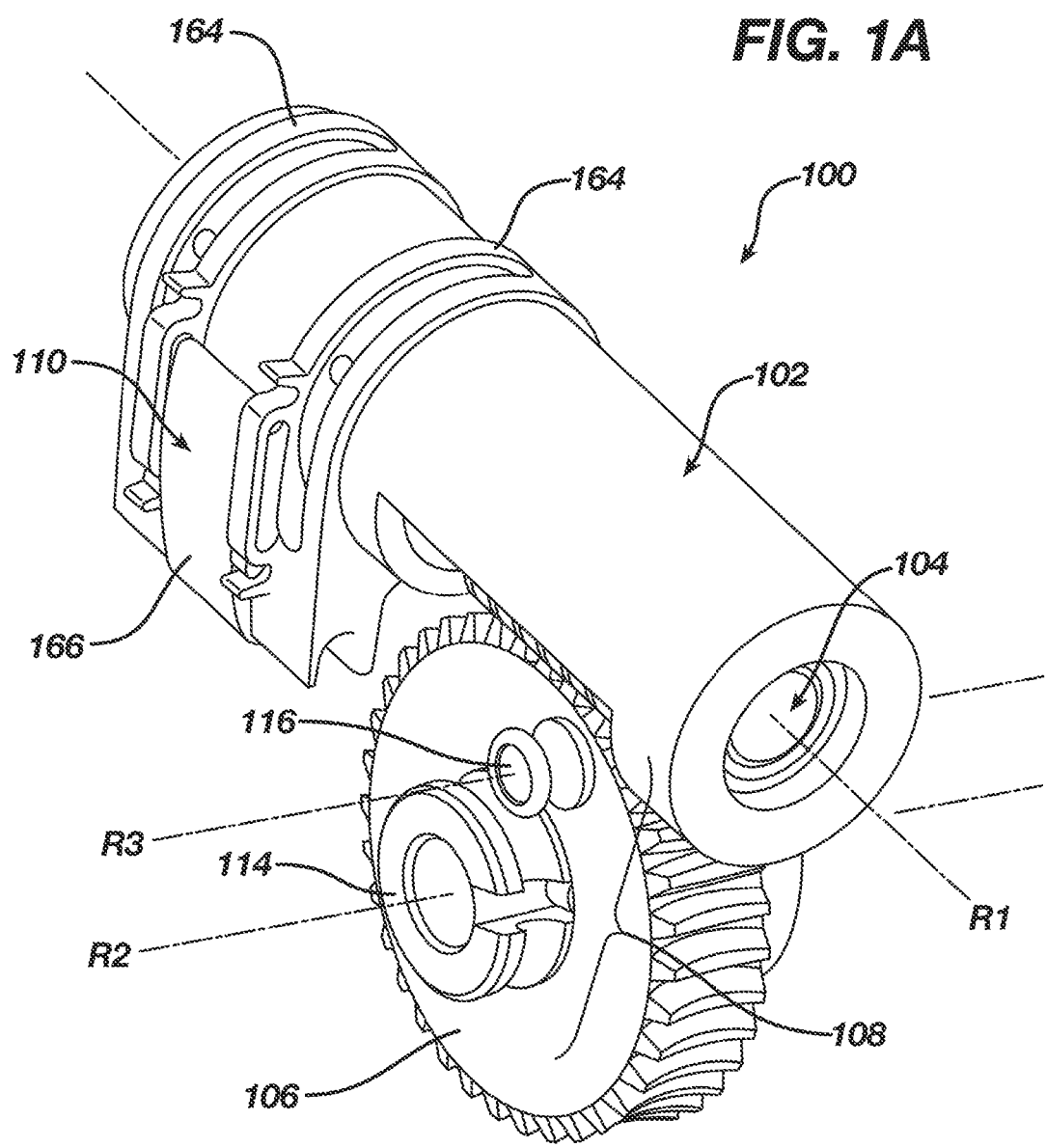
FIG. 1A is a perspective view of an instrument for cutting and bending an implant.

FIGS. 1A-1P illustrate an exemplary embodiment of an instrument 100 which can be used to bend an implant or another object, for example, an implantable spinal rod. As shown, the instrument 100 can include a chassis 102, a drive shaft 104, a worm gear 106, a first rod holder 108 rotatably mounted to the chassis, a second rod holder 110 fixed to the chassis, and a cutting plate 112. The first rod holder 108 can include a main roller 114 and a secondary roller 116. In use, a rod can be positioned between the main roller 114 and the secondary roller 116, while being held in place by the second rod holder 110. The drive shaft 104 can be driven to rotate the worm gear 106 and cause the secondary roller 116 to orbit the main roller 114. As the secondary roller 116 orbits the main roller 114, a bending force can be applied to the rod to bend the rod to a desired degree at a chosen location. The instrument 100 can also be used to cut the rod. For example, the rod can be inserted through an axle portion of the worm gear 106 and through the cutting plate 112, and the drive shaft 104 can be rotated to turn the worm gear with respect to the cutting plate, thereby applying a shear force to the rod to cut or sever the rod.

The chassis 102 can serve as the main body of the instrument 100 to which other components are coupled. The chassis 102 can define a central lumen in which the drive shaft 104 is rotatably disposed. A retention ring or washer 118 can be mounted in corresponding grooves formed in the drive shaft 104 and the interior of the chassis 102 to maintain the drive shaft at a fixed longitudinal position with respect to the chassis. Alternatively, or in addition, the chassis 102 can include an end cap 120 for holding the drive shaft 104 within the chassis.

A proximal end of the chassis 102 can include a mating feature for coupling the instrument 100 to a driver tool (e.g., a manual, electric, hydraulic, or pneumatic drill or driver tool). An exemplary battery-powered driver tool 400 is shown coupled to the instrument 100 in FIGS. 1D and 1s described further below with respect to FIG. 4. The illustrated chassis 102 is configured for use with a driver tool that includes a rotating component sized to fit within a proximal cylindrical opening of the chassis to engage a drive feature 122 formed at the proximal end of the drive shaft 104. The chassis 102 is non-rotatably coupled to a non-rotating component of the driver tool. Accordingly, when the driver tool is actuated, the drive shaft 104 rotates relative to a handle portion of the driver tool while the chassis 102 remains stationary with respect to the handle portion of the driver tool. The chassis 102 can include one or more pins or other anti-rotation features to prevent the chassis from rotating relative to the driver tool. The chassis 102 can include a chassis extension 124 to which the worm gear 106 can be rotatably mounted. The chassis extension 124 can be disposed at the distal end of the chassis 102 and can extend radially outward therefrom.

Figure 1B:
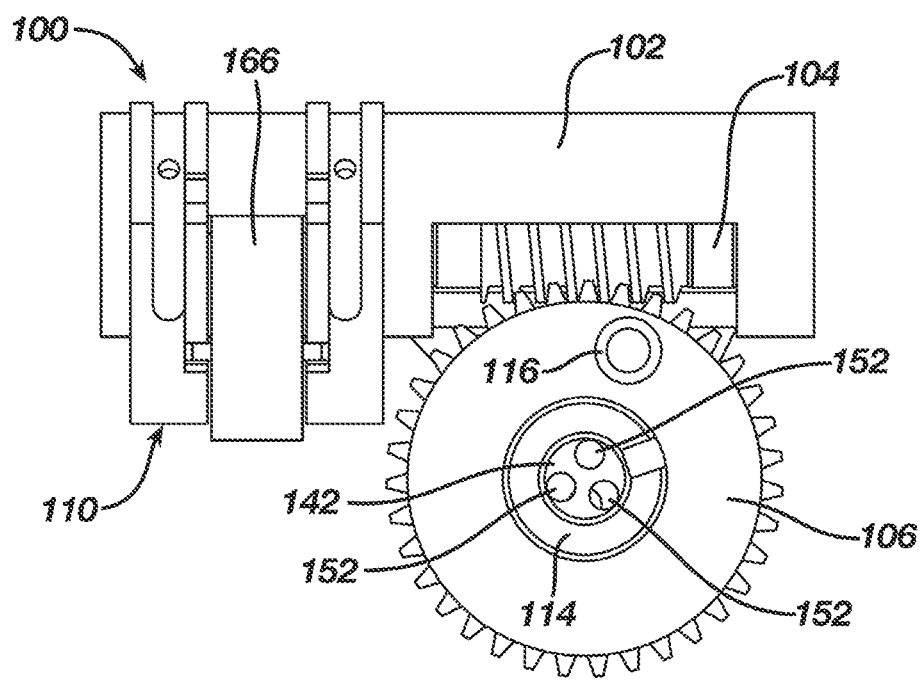
FIG. 1B is profile view of the instrument of FIG. 1A.

The drive shaft 104 can be an elongate cylindrical rod having proximal and distal ends. In operation, the drive shaft 104 can rotate about a rotation axis R1. The drive shaft 104 can include a threaded portion or worm screw 126. The worm screw 126 can be formed integrally with the drive shaft 104. In the illustrated embodiment, however, the worm screw 126 is formed as a separate sleeve component in which the drive shaft 104 is received. The longitudinal position of the worm screw 126 with respect to the drive shaft 104 can be fixed by first and second retaining caps 128. As shown in FIG. 1F, at least one of the retaining caps 128 can be formed integrally with the drive shaft 104. The rotational position of the worm screw 126 with respect to the drive shaft 104 can be fixed by an elongated tab or key 130 that sits within corresponding grooves formed in the exterior surface of the drive shaft and the interior surface of the worm screw 126.

The drive shaft 104 can be mounted in proximal and distal bearing assemblies disposed within the chassis 102 to facilitate rotation of the drive shaft relative to the chassis. As shown in FIG. 1F, the first and second retaining caps 128 can include reduced-diameter shaft portions 132 over which the bearing assemblies are mounted. While any of a variety of bearing assemblies can be used, the illustrated bearing assemblies are race bearings that include an outer race 134, an inner race 136, and at least one ball bearing 138 disposed within respective annular tracks formed in the outer and inner races. The race bearings can also include proximal and distal retaining washers 140. The outer races 134 can be press fit or otherwise coupled to the chassis 102 and the inner races 136 can be press fit or otherwise coupled to the retaining caps 128 such that rotation of the drive shaft 104 relative to the chassis 102 causes the inner race 136 to rotate relative to the outer race 134, with the ball bearing 138 reducing the friction associated with said rotation.

The worm gear 106 can have a plurality of teeth formed on an exterior circumferential surface thereof. The teeth of the worm gear 106 can engage the threaded portion of the drive shaft 104 such that the rotation of the drive shaft 104 about the axis R1 causes the worm gear to rotate about its central axis R2. As shown in FIG. 1A, the axis R2 can extend substantially perpendicular to a plane in which the axis R1 lies. The worm gear 106 and the drive shaft 104 can form a worm drive in which the teeth of the worm gear 106 form the worm wheel and the threaded portion 126 of the drive shaft 104 forms the worm screw. The size, number, and spacing of the teeth, as well as the size of the worm gear 106, can be selected to increase or decrease the torque applied to the worm gear 106 or the rotating speed of the worm gear 106.

As noted above, the instrument can include a first rod holder 108 defined by a main roller 114 and a secondary roller 116.

Figure 1C:
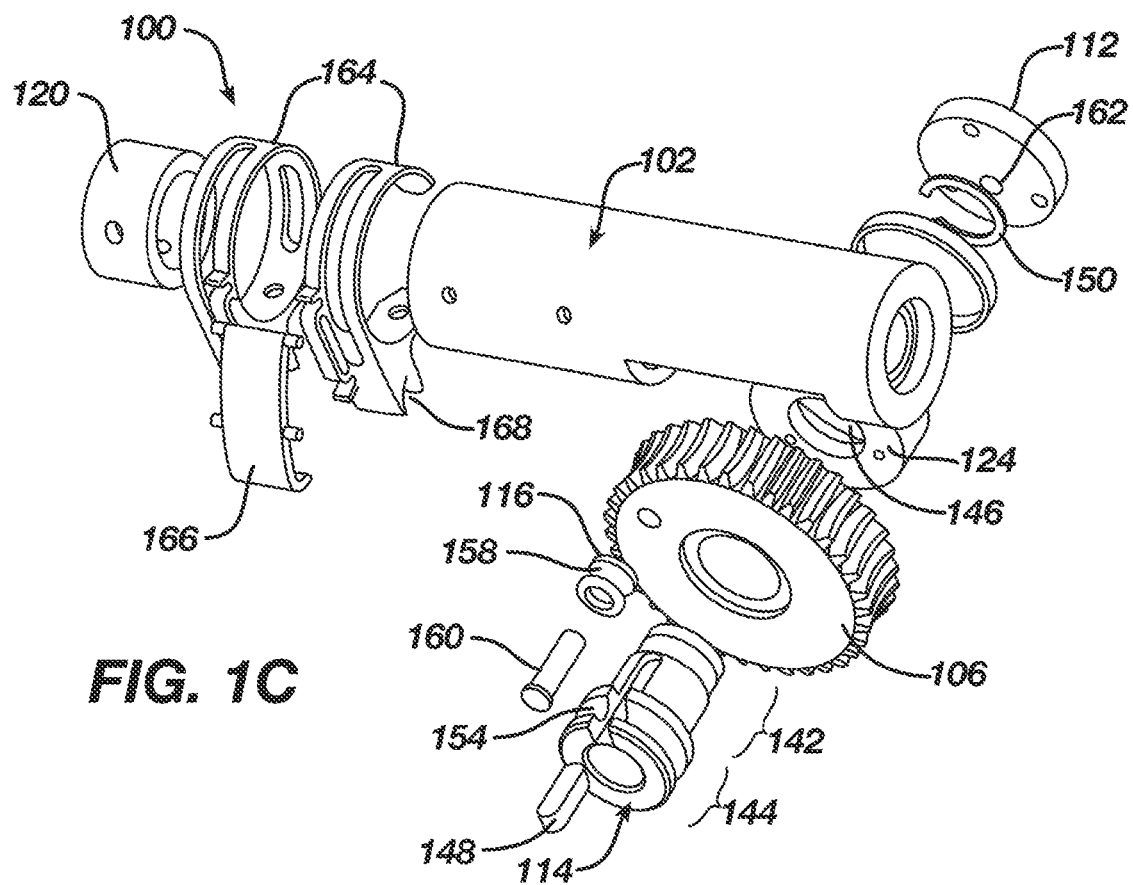
FIG. 1C is an exploded perspective view of the instrument of FIG. 1A.
Figure 1D:
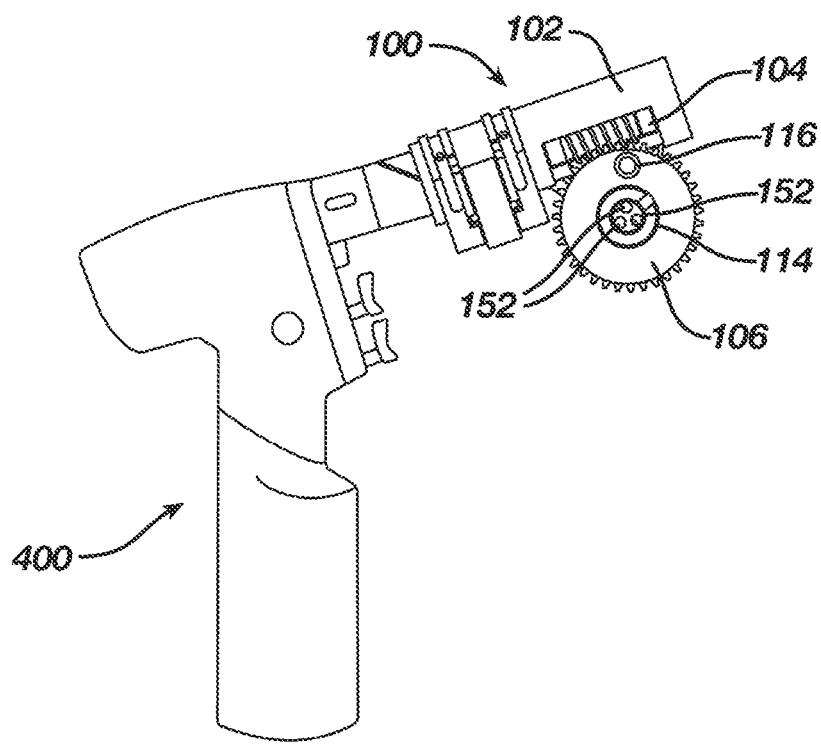
FIG. 1D is a profile view of the instrument of FIG. 1A coupled to a driver tool.
Figure 1E:
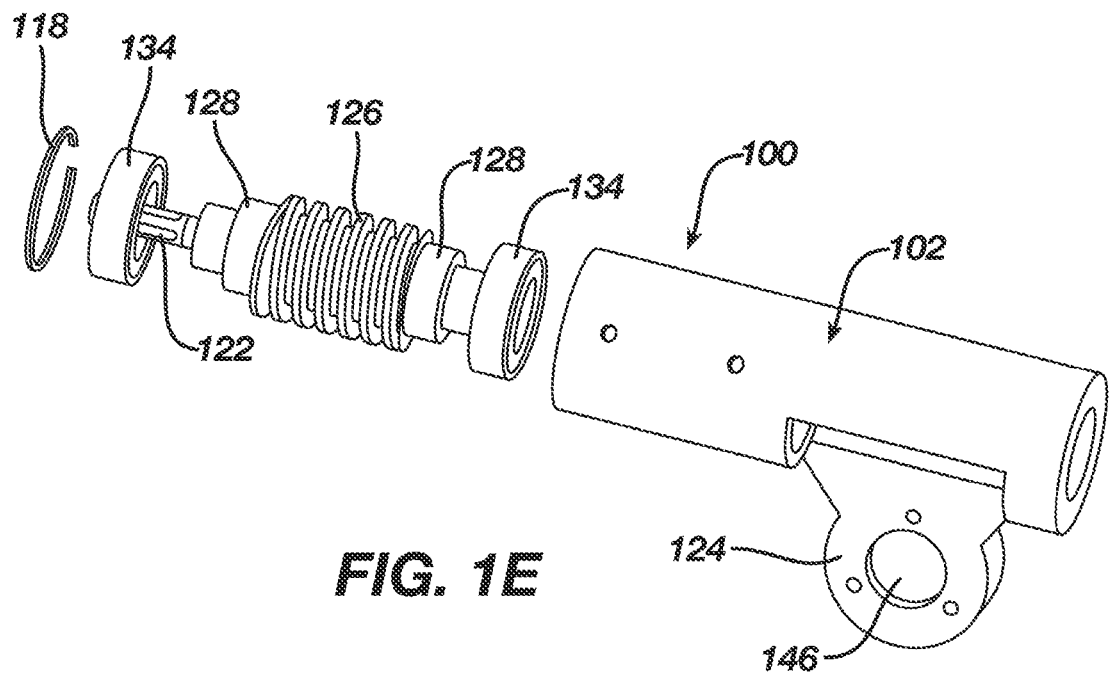
FIG. 1E is an exploded perspective view of the chassis of the instrument of FIG. 1A.
Figure 1F:
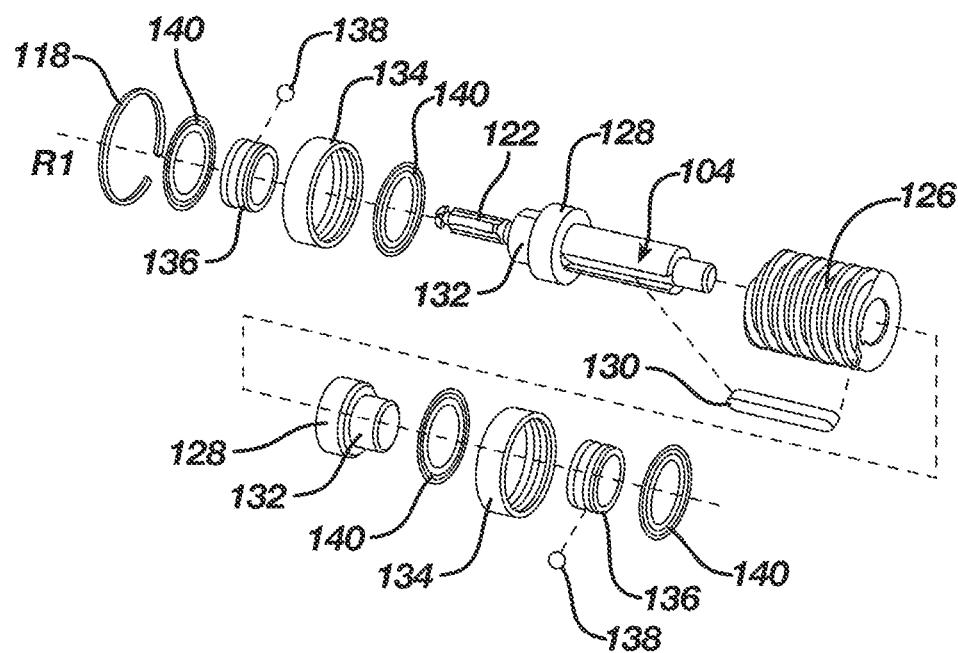
FIG. 1F is an exploded perspective view of the drive shaft of the instrument of FIG. 1A.

As shown in FIG. 1C, the main roller 114 can include an axle portion 142 and a roller portion 144. The axle portion 142 can be rotatably mounted in an opening 146 formed in the chassis 102. The main roller 114 can be rotationally fixed to the worm gear 106. For example, an elongated tab or key 148 can sit within corresponding grooves formed in the exterior surface of the main roller and the interior surface of the worm gear 106 to lock the main roller to the worm gear. Alternatively, the worm gear 106 can be formed integrally with the main roller 114, or can be configured to rotate relative to the main roller. A circlip or other retaining member 150 can be seated within a groove formed in the axle portion 142 to retain the axle portion within the opening 146 formed in the chassis 102. The axle portion 142 can include at least one hole or through-bore 152 in which an implant can be received. For example, as shown in FIG. 1B, the axle portion 142 can include three through-bores 152. It will be appreciated that the axle portion 142 can include any number of through-bores for receiving an implant therethrough. As described further below, the openings 152 formed in the axle portion 142 can allow the axle portion to act as a cutting wheel for cutting an implant extending through the axle portion and through the cutting plate 112.

The roller portion 144 of the main roller 114 can be disposed at the center of the worm gear 106 or can be offset from the center of the worm gear. The roller portion 144 can be formed integrally with the axle portion 142 of the main roller 114, or can be a separate component selectively attached to the axle portion and/or to the worm gear 106. The roller portion 144 can be configured to rotate about its central axis with respect to the worm gear 106, or can be rotationally-fixed with respect to the worm gear.

The roller portion 144 can include an annular recess or groove 154 that defines a bending surface for contacting a rod disposed between the main roller 114 and the secondary roller 116. The groove 154 can have a cross-sectional shape that forms a section of a circle, as shown, or can have various other cross-sectional shapes, such as oval, oblong, square, triangular, and so forth. In some embodiments, the cross-sectional shape of the groove 154 can correspond with the cross-sectional shape of an implant that is to be bent by the instrument 100. The diameter of the groove 154 can be varied to support bending of rods having different diameters.

The roller portion 144 and/or the entire main roller 114 can be interchangeable. This can allow the roller portion 144 to be removed from the instrument 100 and replaced with another roller portion having a different geometry, e.g., a different diameter, groove shape, or the like. Varying the geometry of the roller portion 144 can alter the degree or shape of the resulting bend formed in the rod. For example, a main roller 114 that has a larger diameter can produce a more gradual bend than a main roller with a smaller diameter. The instrument 100 can be provided as part of a kit that includes a plurality of roller portions 144, each having a different geometry. In use, the roller portion 144 having the geometry necessary for forming the desired bend can be selected from the kit and coupled to the instrument 100 for bending the rod.

Figure 1G:
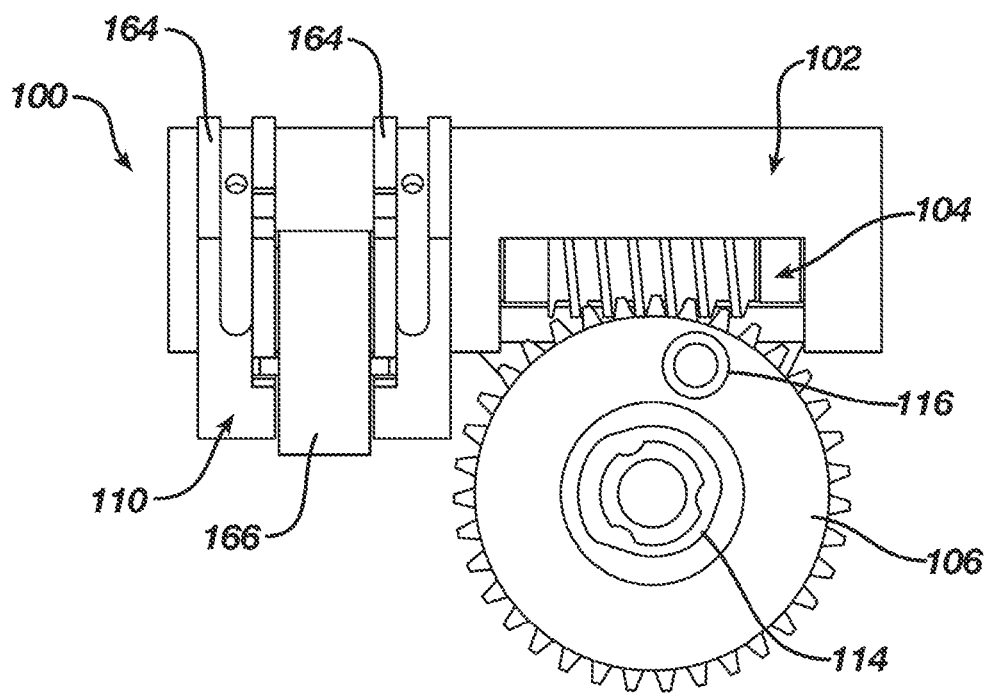
FIG. 1G is a profile view of the instrument of FIG. 1A with a multi-radius main roller.
Figure 1H:
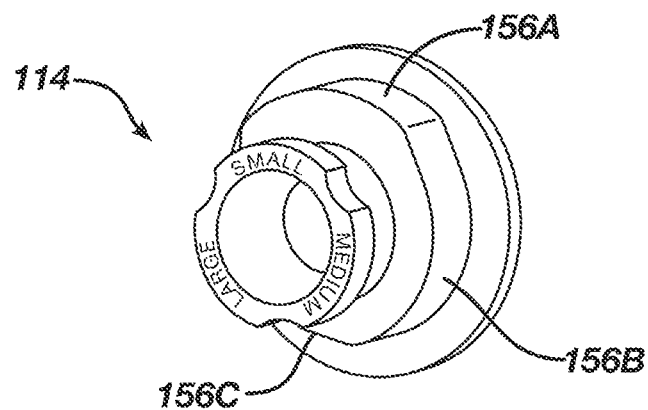
FIG. 1H is a perspective view of the multi-radius main roller of FIG. 1G.
Figure 1I:
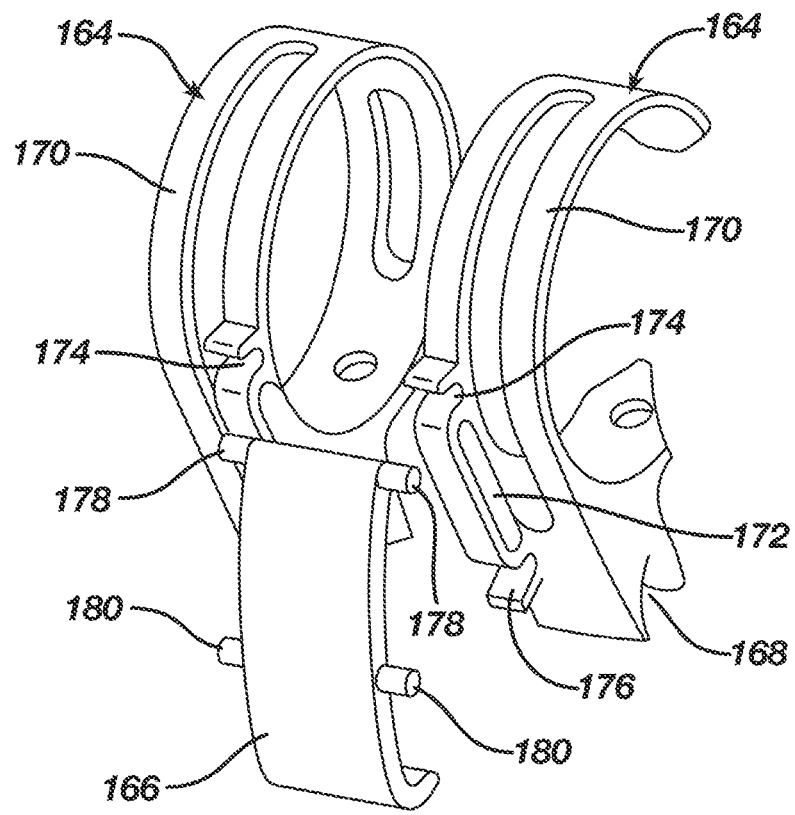
FIG. 1I is an exploded perspective view of a rod holder of the instrument of FIG. 1A.

A single main roller 114 can also have a geometry that varies along its circumference such that the same main roller can be used to form multiple types of bends. For example, a single main roller 114 can include two or more varying radii of curvature. As illustrated in FIGS. 1G and 1H, a multi-radius main roller 114 can include two or more arcuate portions 156, each arcuate portion having a different radius of curvature. A multi-radius main roller 114 can allow the user to select an arcuate portion 156 that can achieve a specific degree of bending in a rod without replacing the main roller in the device 100. The multi-radius main roller 114 can have any number of arcuate portions 156 to provide the user with options for bending a rod. As illustrated in FIG.

1H, a multi-radius main roller 114 can include three arcuate portions 156A, 156B, 156C, each arcuate portion having a progressively larger radius of curvature.

In some embodiments, the main roller 114 can have an adjustable outer diameter that can be expanded or contracted with manipulation by the user. For example, a main roller 114 can include concentric circular portions of varying diameters and can be moved relative to the worm gear 106 to position a portion having the desired diameter in contact with the rod.

The secondary roller 116 can include an annular recess or groove 158 formed therein that defines a bending surface for contacting a rod disposed between the main roller 114 and the secondary roller 116. The groove 158 can thus engage an opposite side of a rod that is disposed within the groove 154 of the main roller 114. The secondary roller 116 can be mounted to the worm gear 106 such that the secondary roller orbits the main roller 114 when the worm gear rotates. The secondary roller 116 can be positioned relative to the main roller 114 so as to allow a rod positioned therebetween to contact the main roller 114 and the secondary roller 116 simultaneously.

The secondary roller 116 can be rotatably mounted to the worm gear 106 such that it can rotate about its central axis R3 with respect to the worm gear. Alternatively, the secondary roller 116 can be rotationally-fixed relative to the worm gear. In the illustrated embodiment, the secondary roller 116 is secured to the surface of the worm gear 106, though the secondary roller can also be elevated such that it is offset from the surface of the worm gear. The secondary roller 116 can be mounted to the worm gear 106 by a pivot pin 160 that extends through a central bore of the secondary roller. The secondary roller 116 can have varying geometries and a variety of different secondary rollers can be interchangeably coupled to the instrument 100, in the same manner as described above with respect to the main roller 114.

The cutting plate 112 can be formed integrally with the chassis 102 or can be coupled thereto as shown. As shown in FIG. 1C, the cutting plate 112 can include a disc-shaped plate having at least one opening 162 formed therein in which a rod to be sheared or cut can be received. Any of a variety of techniques can be used to attach the cutting plate 112 to the chassis 102. For example, the cutting plate 112 can include one or more openings in which a screw or bolt can be received to secure the cutting plate to the chassis 102. The cutting plate 112 can be rotationally fixed relative to the chassis 102.

To cut an implant, the main roller 114 can be positioned such that at least one of the openings 152 formed therein is aligned with the opening 162 of the cutting plate 112. An implant (e.g., a spinal rod) that is to be cut can be inserted through the opening 152 of the main roller 114 and through the opening 162 formed in the cutting plate 112. A user can then actuate a driver tool to which the instrument 100 is coupled to rotate the drive shaft 104 and the worm screw 126. Rotation of the worm screw 126 can cause the worm gear 106 to rotate relative to the chassis 102 and relative to the cutting plate 112, which is rotationally fixed to the chassis 102. Accordingly, the sidewalls of the openings 152, 162 exert a shear force on the rod inserted therethrough, cutting or severing the rod. In some embodiments, the sidewalls of one or more of the openings 152, 162 can be tapered or ramped to provide sharpened portion(s) (e.g., at the cutting interface between the worm gear 106 and the plate 112).

The openings 152, 162 formed in either the worm gear 106 or the cutting plate 112 can be elongated to further increase the number of rotational positions of the worm gear at which the opening 152 is aligned with an opening 162 of the cutting plate. The openings 152 can have any of a variety of other shapes (e.g., trapezoidal, ramped or blade-shaped, bean-shaped, etc.). The openings in the cutting plate 112 can be elongated instead, or in addition to the openings in the worm gear 106. The worm gear 106 and/or the cutting plate 112 can include rod openings of various sizes to facilitate use of the instrument with rods having various sizes (e.g., rods having different diameters). As noted above, the cutting plate 112 can be formed integrally with the chassis 102. In other words, the cutting plate 112 can be omitted and the chassis 102 itself can serve as the cutting plate. Further details on cutting and other features that can be included in the instrument 100 are disclosed in U.S. Pat. No. 10,076,376, filed on May 27, 2015, entitled "DEVICES AND METHODS FOR BENDING OR CUTTING IMPLANTS," which is hereby incorporated herein by reference in its entirety.

The second rod holder 110 can be configured to hold at least a portion of a rod that is to be bent in a fixed position relative to the chassis 102. An exemplary rod holder 110 is shown in detail in FIGS. 1I-1M. As shown, the rod holder 110 can include one or more mounts 164 and a lid 166. The lid 166 can be pivoted relative to the mounts 164 between a first, open position (shown in FIGS. 1J-1K) and a second, closed position (shown in FIGS. 1L-1M). In the open position, the lid 166 is pivoted away from the mounts 164 to allow a rod to be introduced into rod seats 168 formed in each of the mounts. In the open position, a rod that is to be bent can be free to translate and/or rotate with respect to the rod holder 110. In the closed position, the lid 166 can be closed over a rod that is to be bent, such that the lid holds the rod in contact with the rod seats 168. In the closed position, the rod holder 110 can restrict or prevent translation and/or rotation of the rod relative to the chassis 102.

Each mount 164 can include a rod seat 168, an engagement portion 170 for securing the mount to the chassis 102, and features for allowing the lid 166 to pivot relative to the mount and to be secured in either the locked position or the released position. In the illustrated embodiment, these features include an elongate slot 172 and first and second recesses 174, 176 disposed at opposite ends of the slot.

The rod seat 168 can be defined by opposed arms that define a rod-receiving recess therebetween. The rod seat 168 can be oriented at various angles with respect to the chassis 102, but in the illustrated embodiment, the rod seat is positioned such that a portion of a rod disposed therein has a central longitudinal axis that is parallel to the central longitudinal axis R1 of the chassis 102.

The engagement portion 170 can be a ring-shaped strap that secures the mount 164 to the chassis 102. The engagement portion 170 can be configured to receive the chassis 102 therethrough, such that the engagement portion extends around at least a portion of the circumference of the chassis. One or more openings can be formed in the engagement portion 170 to receive a pin, detent, or other feature for securing the engagement portion to the exterior surface of the chassis 102. Alternatively, or in addition, the mount 164 can be attached to the chassis 102 by a screw, bolt, press-fit, snap-fit, magnet, weld, strap, clamp, or the like. While two mounts 164 are shown, the rod holder 110 can include any number of mounts for attaching the rod holder to the chassis 102.

The lid 166 can include a first end and a second end. The first end of the lid 166 can include opposed pivot pegs 178. The pegs 178 can extend laterally outward from the sidewalls of the lid 166. The pegs 178 can be slidably and rotatably received in the slots 172 formed in the mounts 164, such that the lid 166 can pivot with respect to the mounts about a central axis of the pegs 178 and such that the lid can translate with respect to the mounts by sliding the pegs within the slots.

The second end of the lid 166 can be configured to capture a rod between the lid and the rod seats 168 of the mounts 164. The second end of the lid 166 can be curved as shown, such that the underside of the lid defines a semi-cylindrical rod seat. The second end of the lid 166 can include opposed locking pegs 180. The pegs 180 can extend laterally outward from the sidewalls of the lid 166. The locking pegs 180 can be received within the first recesses 174 or the second recesses 176 of the mounts 164 to secure the lid in the open position or the closed position, respectively.

Figure 1J:
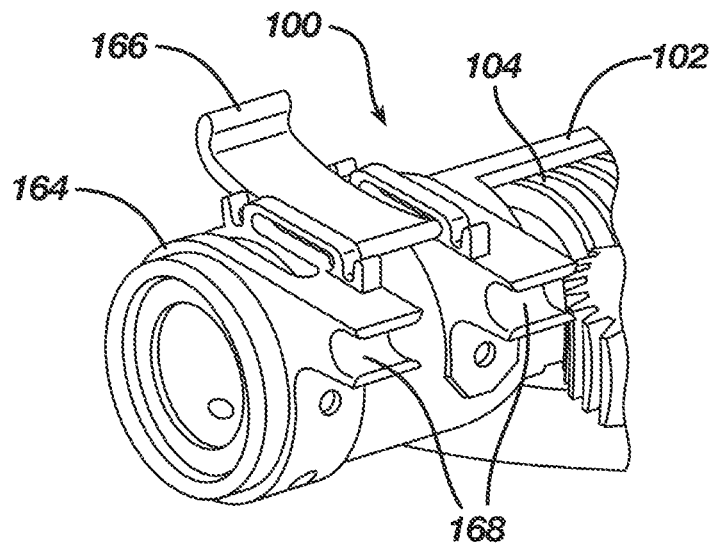
FIG. 1J is a perspective view of the rod holder of FIG. 1I in an open configuration.
Figure 1K:
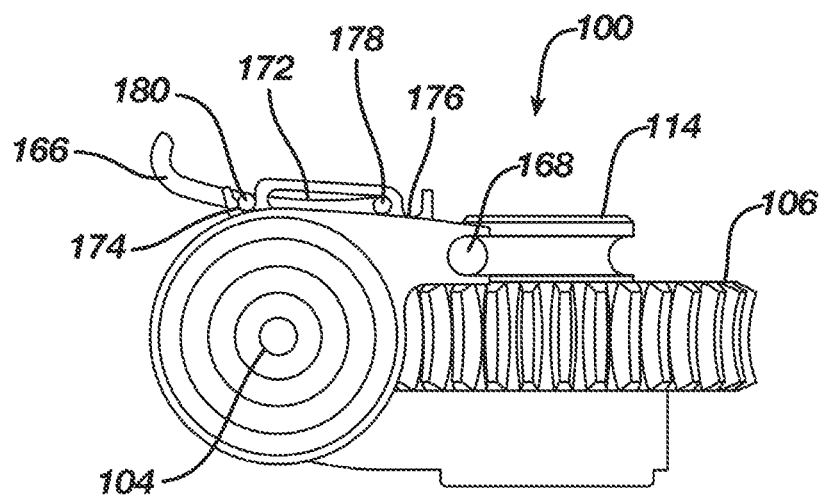
FIG. 1K is a profile view of the rod holder of FIG. 1I in the open configuration.
Figure 1L:
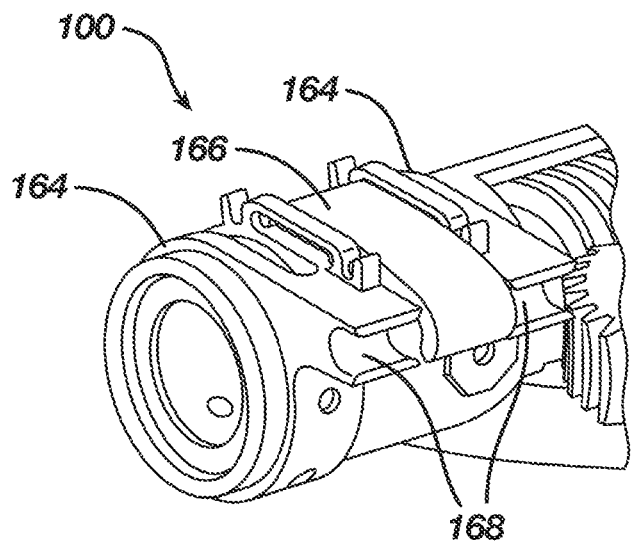
FIG. 1L is perspective view of the rod holder of FIG. 1I in a closed configuration.
Figure 1M:
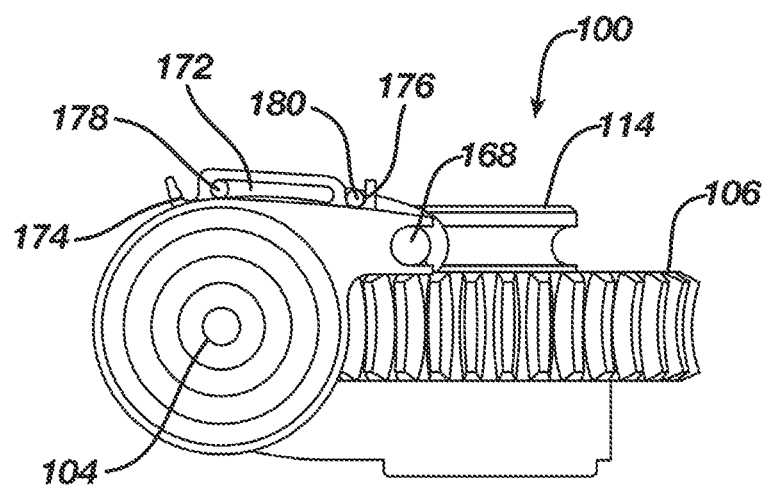
FIG. 1M is profile view of the rod holder of FIG. 1I in the closed configuration.

As shown in FIGS. 1J-1K, the lid 166 can be moved to the open position by rotating the lid about the axis of the pivot pegs 178 and sliding the pivot pegs to a bottom end of the slot 172. The lid 166 can be maintained in the open position by seating the locking pegs 180 within the first recesses 174 of the mounts 164. As shown in FIGS. 1L-1M, the lid 166 can be moved to the closed position by rotating the lid about the axis of the pivot pegs 178 and sliding the pivot pegs to a top end of the slot 172. The lid 166 can be maintained in the closed position by seating the locking pegs 180 within the second recesses 176 of the mounts 164.

Use of the instrument 100 to bend a rod R is shown in FIGS. 1N-1P. In the example shown, an initially straight rod R is to be bent such that a distal portion of the rod extends at an oblique angle with respect to a proximal portion of the rod. It will be appreciated that the instrument 100 can be used to form bends having different shapes, and can form bends in rods that already have one or more bends formed therein.

As shown in FIG. 1N, the rod R can be secured to the instrument 100 using the first and second rod holders 108, 110. In particular, a distal portion of the rod R can be positioned between the main and secondary rollers 114, 116 of the first rod holder 108. The rod R can be longitudinally translated and/or axially rotated to position a portion of the rod where the inner bend radius is to be formed against the annular groove 154 of the main roller 114, and to position a portion of the rod where the outer bend radius is to be formed against the annular groove 158 of the secondary roller 116. In the illustrated embodiment, the rod R is in contact with both the main roller 114 and the secondary roller 116, though a gap can exist between the rod and the rollers before and/or after the rod is bent. Further, as previously discussed, the main roller 114 can be rotated, adjusted, and/or replaced with another roller to vary the shape and/or radius of the resulting bend in the rod.

Once the rod R is positioned as needed to achieve the desired bend, a proximal portion of the rod can be secured to the second rod holder 110. The lid 166 (not shown in FIGS. 1N-1P for clarity) of the second rod holder 110 can be positioned initially in the open position of FIGS. 1J-1K and the rod R can be seated in the rod seats 168 of each mount 164. The lid 166 can then be moved to the closed position of FIGS. 1L-1M to capture the rod R between the lid and the rod seats 168, thereby restricting or preventing movement of the rod with respect to the chassis 102.

As shown in FIG. 1O a driver tool to which the instrument 100 is coupled can be actuated to rotate the drive shaft 104 about the axis R1. Rotation of the drive shaft 104 can cause the worm gear 106 to rotate about the axis R2, thereby causing the secondary roller 116 to orbit the main roller 114 in the direction of arrow D1 to form a bend in the rod R.

After bending the rod R, as shown in FIG. 1N, the driver tool can be actuated to rotate the drive shaft 104 in the opposite direction, thus causing the secondary roller 116 to orbit the main roller 114 in the direction of arrow D2. This can allow the secondary roller 116 to be moved out of engagement with the rod R, e.g., to allow the bent rod to be removed from the instrument 100.

The steps above can be repeated any number of times with the instrument 100 being repositioned along the rod R as needed to form any number of bends in the rod. The instrument 100 can include markings or indicia for displaying to the user the degree to which the rod R has been bent. For example, a series of bend angle markings can be printed, engraved or otherwise formed on the worm gear 106 to illustrate to the user the degree of bending.

FIGS. 2A-2J illustrate another exemplary embodiment of an instrument 200 for bending and/or cutting an implant. Except as indicated below and as will be readily appreciated by one having ordinary skill in the art, the structure and function of the instrument 200 is substantially the same as that of the instrument 100 described above, and therefore a detailed description is omitted here for the sake of brevity.

As shown, the first rod holder 208 can include a first half-pipe instead of or in addition to the orbiting rollers described above. As also shown, the second rod holder 210 can include a second half-pipe instead of or in addition to the lid-type rod holder described above. While not shown, various combinations of these features can also be used. For example, a half-pipe rod holder can be used to secure the rod to the chassis 202 and an orbiting roller rod holder can be used to secure the rod to the worm gear 206. By way of further example, a lid-type rod holder can be used to secure the rod to the chassis 202 and a half-pipe rod holder can be used to secure the rod to the worm gear 206.

Figure 2A:
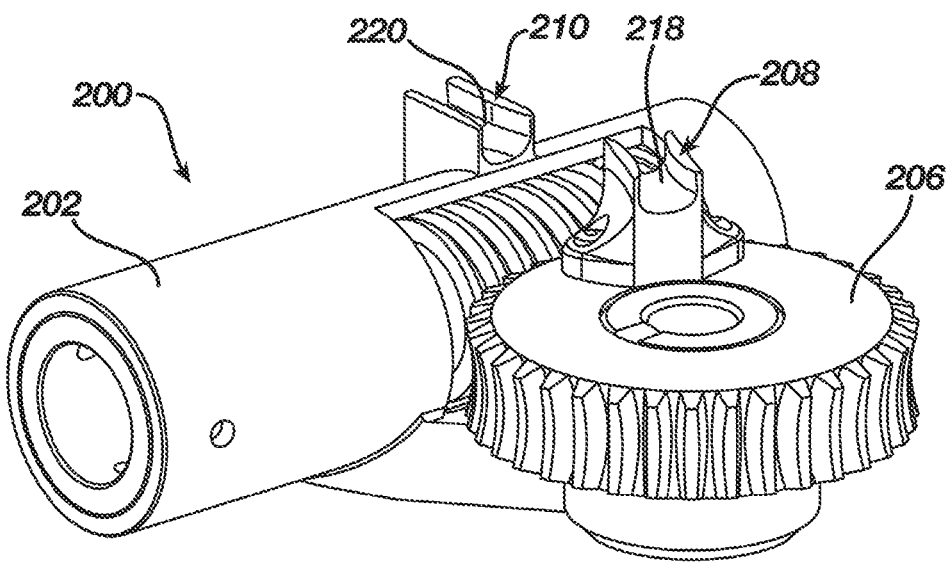
FIG. 2A is a perspective view of an instrument for cutting and bending an implant.
Figure 2B:
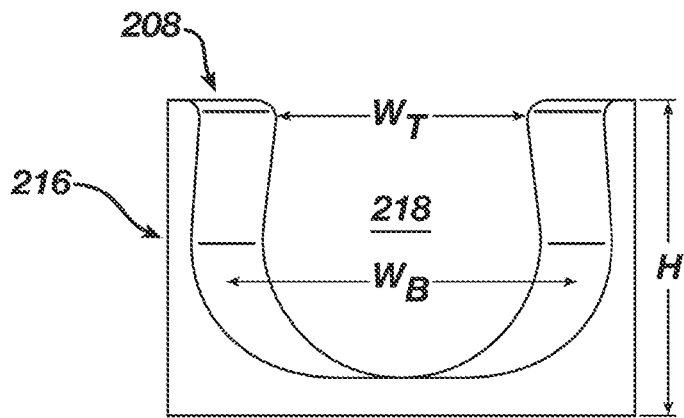
FIG. 2B is a profile view of a half-pipe of the instrument of FIG. 2A.
Figure 2C:
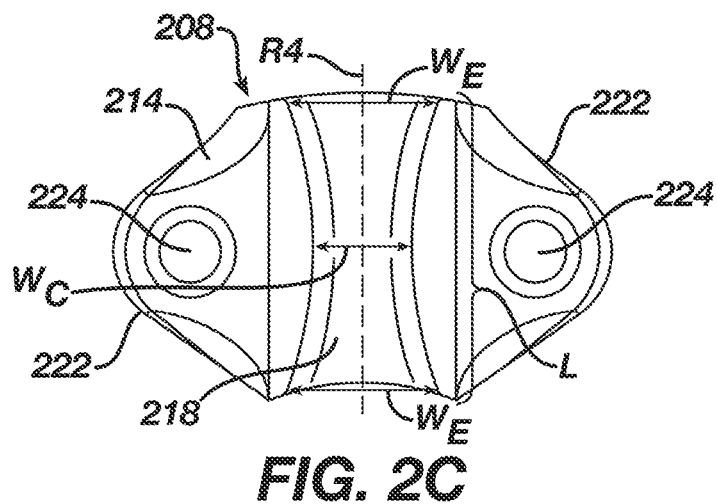
FIG. 2C is a plan view of the half-pipe of FIG. 2B.

The first half-pipe 208 can include a base portion 214 and a top portion 216. The top portion 216 can include opposed arms that define a rod-receiving recess 218 therebetween. The recess 218 can have a central axis R4. As shown in FIG. 2B, the inner surfaces of the arms can taper or curve inward, such that a width $W_T$ of the recess 218 at the free ends of the arms is less than a width WB at the lower portion of the arms where the rod is seated. This can help prevent the rod from slipping out of the half-pipe 208. In some embodiments, the width $W_T$ at the free ends of the arms can be less than the diameter of the rod, such that the arms deflect slightly as the rod is inserted and such that the rod snap-fits into the recess 218. While not shown, the first half-pipe 208 can include a lid, set screw, or other closure mechanism for securing a rod in the recess 218. As shown in FIG. 2C, the recess 218 can have curved longitudinal sidewalls such that the width W of the recess varies along the length L of the recess. The recess 218 can thus have a width We at a central portion of the recess that is less than the width WE of the recess at opposed end portions thereof. The curved sidewalls can allow for a smoother bend to be formed in the rod, can allow a greater degree of bending to be applied to the rod, or can allow a pre-bent rod to be inserted into the recess 218.

The base portion 214 can have an elevated height to align the rod recess 218 of the first half-pipe 208 with a corresponding rod recess 220 of the second half-pipe 210. The base portion 214 can have opposed lateral flanges 222 with openings 224 formed therein for receiving fastening elements 226 to couple the base portion to the worm gear 206.

The fastening elements 226 can be bolts, screws, press-fit pins, or other devices for attaching the base portion 214 to the worm gear 206. The base portion 214 can also be welded to the worm gear 206 or formed integrally therewith. The half-pipe can include fillets 228 extending between the arms of the top portion 216 and the flanges 222 of the base portion 214 to help evenly distribute forces that are imparted on the half-pipe 208.

Figure 2D:
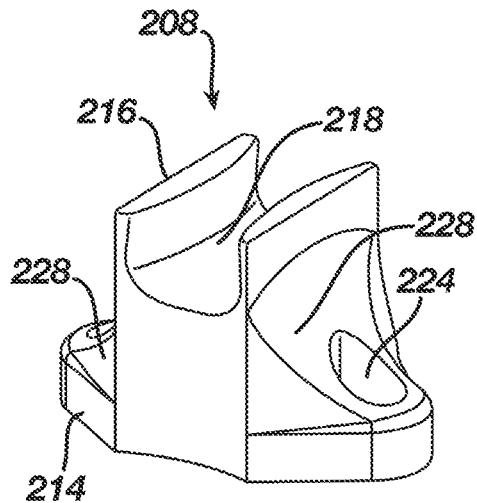
FIG. 2D is a perspective view of a fixed half-pipe that can be used with the instrument of FIG. 2A.
Figure 2E:
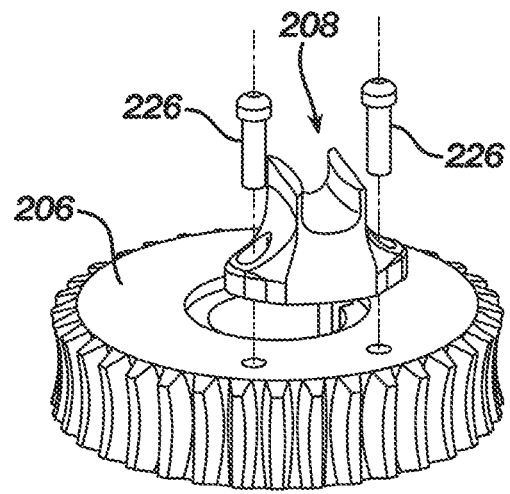
FIG. 2E is an exploded perspective view of the half-pipe of FIG. 2D and a worm gear of the instrument of FIG. 2A.
Figure 2F:
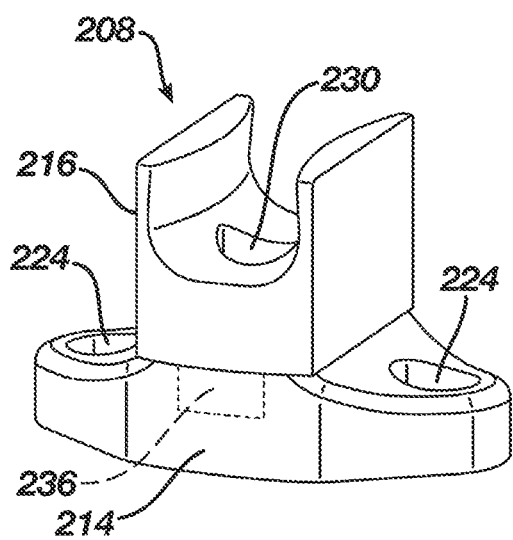
FIG. 2F is a perspective view of a pivoting half-pipe that can be used with the instrument of FIG. 2A.
Figure 2G:
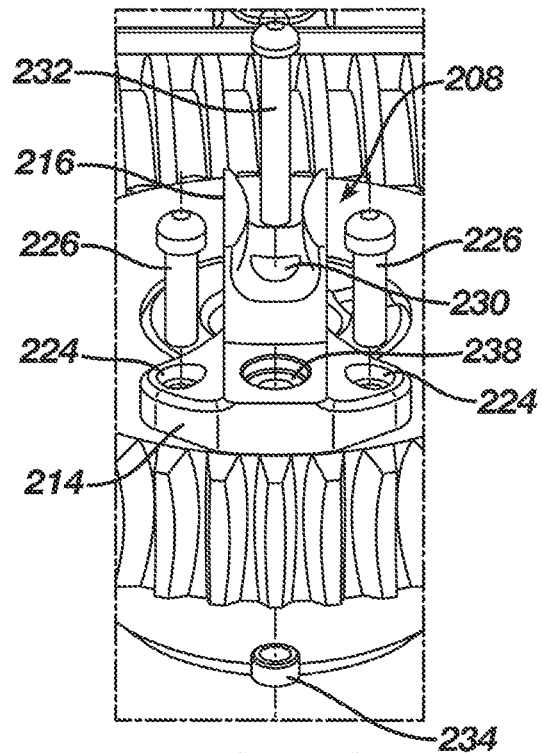
FIG. 2G is an exploded perspective view of the half-pipe of FIG. 2F and a worm gear of the instrument of FIG. 2A.

The base portion 214 and the top portion 216 can be a single, monolithic component, as shown in FIGS. 2D-2E, or can be separate components as shown in FIGS. 2F-2G. In the latter configuration, the base portion 214 can include a throughbore 230 formed therein for receiving a center axle 232 about which the top portion 216 can rotate relative to the base portion. A nut 234 can be threaded onto the center axle 232 to secure the construct to the worm gear 206. The top portion 216 can include a cylindrical protrusion 236 configured to be rotatably received within a corresponding cylindrical recess 238 formed in the base portion 214. This interface can relieve stresses from the center axle 232 and can ensure a secure connection is formed between the top portion 216 and the base portion 214. The center axle 232 can have a diameter that is less than the diameter of throughbore 230, which can create a loose fit between the center axle and the throughbore that allows for smooth pivoting of the top portion 216 relative to the base portion 214.

The second half-pipe 210 can include any of the features of the first half-pipe 208 discussed above, and can be attached to or formed integrally with the chassis 202.

Figure 2H:
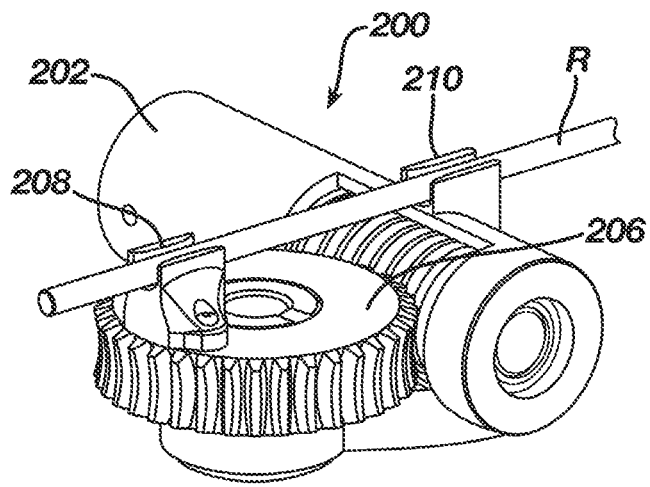
FIG. 2H is a perspective view of the instrument of FIG. 2A having a rod disposed therein prior to actuation.
Figure 2I:
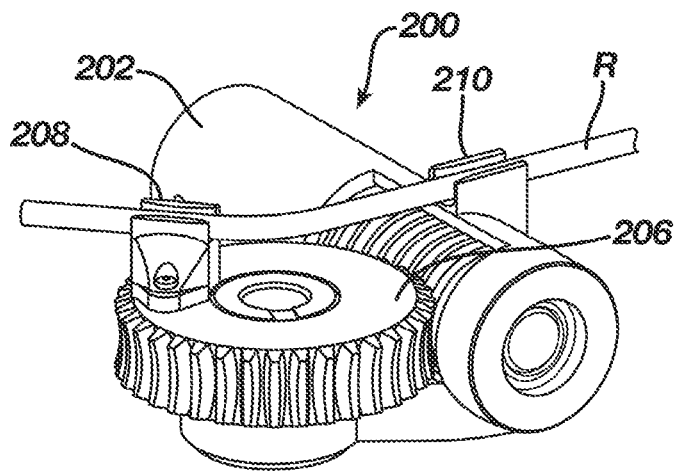
FIG. 2I is a perspective view of the instrument of FIG. 2A bending a rod disposed therein using a fixed half-pipe.
Figure 2J:
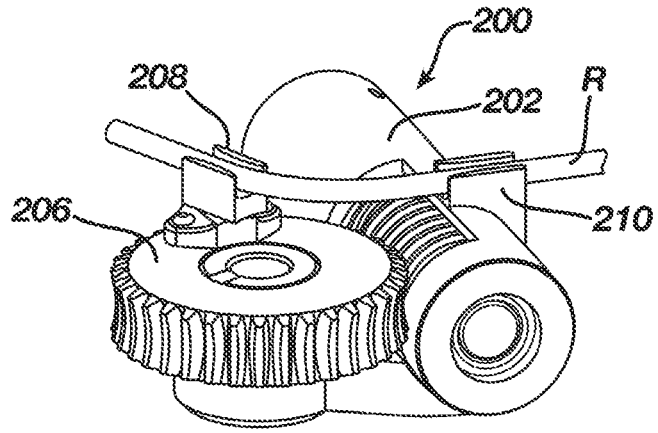
FIG. 2J is a perspective view of the instrument of FIG. 2A bending a rod disposed therein using a pivoting half-pipe.

In use, as shown in FIG. 2H, the worm gear 206 can be rotated to position the half-pipes 208, 210 with respect to one another such that a rod R to be bent can be inserted into both of the half-pipes. Once the rod R is secured within the half-pipes 208, 210, the worm gear 206 can be rotated to form a bend in the rod. FIG. 2I shows a bend being formed in the rod R using the monolithic first half-pipe 208 of FIGS. 2D-2E. FIG. 2J shows a bend being formed in the rod R using the pivoting first half-pipe 208 of FIGS. 2F-2G. The pivoting half-pipe can, in at least some embodiments, allow for a greater degree of bending to be applied to the rod or for a smoother or more gradual bend to be formed as compared with the non-pivoting half-pipe.

Figure 3A:
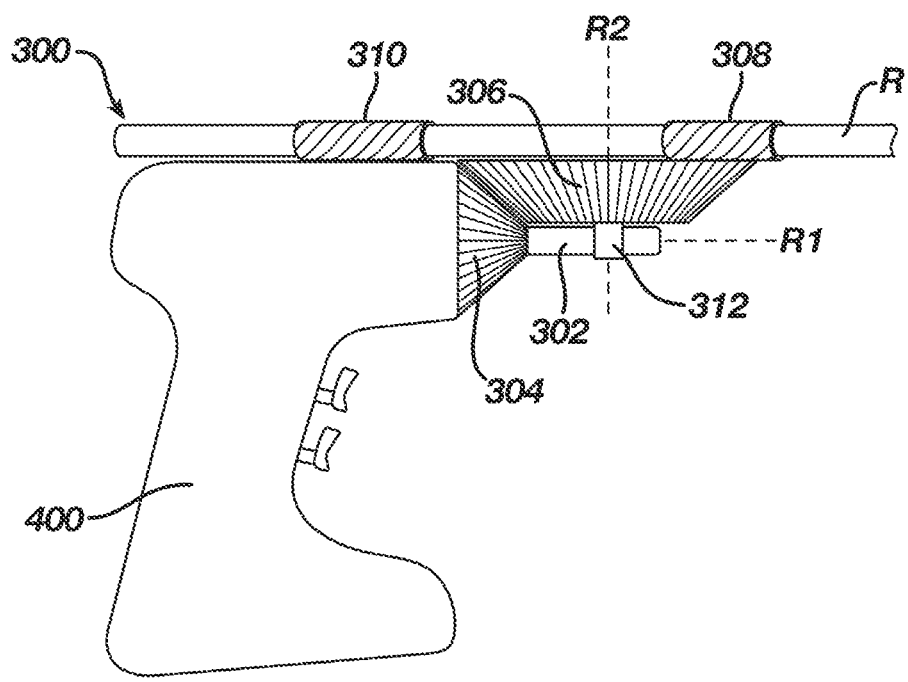
FIG. 3A is a profile view of an instrument for cutting and bending an implant.
Figure 3B:
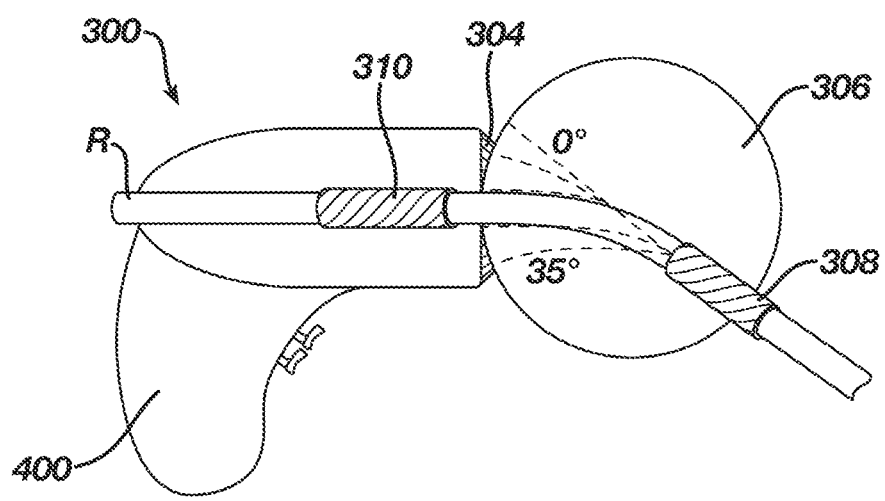
FIG. 3B is a plan view of the instrument of FIG. 3A.

FIGS. 3A-3B illustrate another exemplary embodiment of an instrument 300 for bending and/or cutting an implant. Except as indicated below and as will be readily appreciated by one having ordinary skill in the art, the structure and function of the instrument 300 is substantially the same as that of the instrument 100 described above, and therefore a detailed description is omitted here for the sake of brevity.

As shown for the instrument 300, a conical gear set can be used instead of or in addition to the worm drives described above to convert the rotational input of the driver tool into movement of a first rod holder with respect to a second rod holder. The instrument 300 can include a shaft 302, a first conical gear 304, a second conical gear 306, a first rod holder 308, a second rod holder 310, and an axle 312.

The first conical gear 304 can be rotatably mounted to the shaft 302, such that actuation of a driver tool 400 coupled to the instrument 300 is effective to rotate the first conical gear 304 without rotating the shaft 302. The second conical gear 306 can be rotatably mounted to the axle 312, such that the teeth of the first conical gear 304 and the teeth of the second conical gear 306 are enmeshed. Accordingly, rotation of the first conical gear 340 about an axis R1 can be effective to rotate the second conical gear 306 about an axis R2 that is perpendicular or substantially perpendicular to the axis R1.

The first rod holder 308 can be mounted to the second conical gear 306. The second rod holder 310 can be mounted directly to the driver tool 400 or to an intermediate chassis (not shown). While cylindrical, full-pipe rod holders 308, 310 are shown, it will be appreciated that any of the rod holders described above can be used instead or in addition (e.g., orbiting rollers, lid-type rod holders, pivoting or fixed half-pipe rod holders, and/or combinations thereof).

In use, a rod R can be secured to the instrument 300 using the first and second rod holders 308, 310 and the driver tool 400 can be actuated to rotate the conical gear system 304, 306 to form a bend in the rod. As shown in FIG. 3B, the instrument 300 can include markings or indicia for displaying to the user the degree to which the rod R has been bent. For example, a series of bend angle markings can be printed, engraved or otherwise formed on the second conical gear 306 to illustrate to the user the degree of bending.

Figure 4:
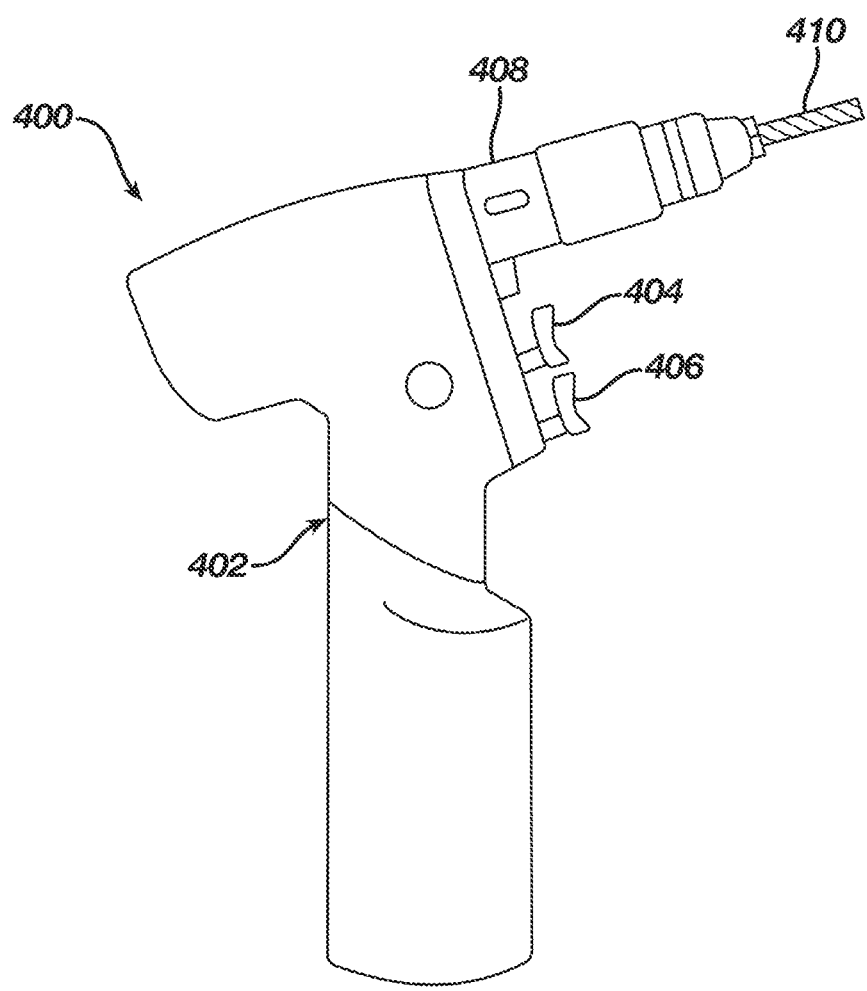
FIG. 4 is a perspective view of a driver tool.

FIG. 4 illustrates an exemplary embodiment of a driver tool 400 that can be used with any of the instruments disclosed herein. The driver tool 400 generally includes a handle portion 402 with first and second actuation buttons 404, 406, a non-rotating mating portion 408 configured to mate the driver tool 400 with a chassis of an instrument (e.g., the instruments 100, 200, 300 described herein), and a rotating component 410 configured to mate with and rotate the drive shaft of an instrument (e.g., the instruments 100, 200, 300 described herein). The rotating component 410 can be driven by a motor and a power source (e.g., a battery) disposed in the driver tool 400. In some embodiments, one of the actuation buttons 404, 406 can be depressed to rotate the rotating component 410 clockwise and the other of the actuation buttons 404, 406 can be depressed to rotate the rotating component counterclockwise. Other exemplary driver tools include the Colibri II System (a compact and modular Li-Ion-battery-driven power tool) available from DePuy Synthes.

It should be noted that while devices and methods for bending or cutting rods are disclosed herein, the instruments 100, 200, 300 can be used to bend various types of orthopedic hardware, for example, plates, cables, implants, etc. It should also be noted that while use of a power driver tool to drive rotation of the instruments is generally contemplated herein, in other embodiments the drive shaft can be rotated manually. Any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

As evident from the foregoing, in at least some embodiments, the instruments disclosed herein can provide one or more advantages as compared with other instruments:

The instruments 100, 200, 300 can provide quicker and more efficient bending and/or cutting of rods.

The instruments 100, 200, 300 can be small and portable which can allow them to be brought closer to the patient and surgical site to bend or cut a rod without leaving the patient or to bend or cut a rod that is at least partially implanted in the patient.

The instruments 100, 200, 300 can be driven by power tools and can require less input force, reducing surgeon fatigue and strength requirements.

The instruments 100, 200, 300 can allow for precise and repeatable bending of rods.

The instruments 100, 200, 300 can allow for bending of rods to a desired shape in fewer iterations, reducing the risk of lowered rod fatigue strength.

The instruments disclosed herein can be constructed from any of a variety of known materials. Exemplary materials include those which are suitable for use in surgical applications, including metals such as stainless steel, polymers such as PEEK, ceramics, carbon fiber, and so forth. The various components of the instruments disclosed herein can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of bending a rod or bone plate in spine or trauma surgery, it will be appreciated that the methods and devices disclosed herein can be used with any human or animal implant, in any of a variety of surgeries performed on humans or animals, and/or in fields unrelated to implants or surgery.

Although specific embodiments are described above, it should be understood that numerous changes may be made within the spirit and scope of the concepts described. Accordingly, it is intended that this disclosure not be limited to the described embodiments, but that it have the full scope defined by the language of the following claims.

The invention claimed is:

1. An instrument for bending an implant, comprising:
    a chassis extending from a proximal end to a distal end to define a length therebetween;
    a first gear rotatably mounted to the chassis;
    a first rod holder mounted onto the first gear and configured to receive a first portion of the implant therein; and
    a second rod holder mounted onto the chassis and configured to receive a second portion of the implant therein,
    wherein the rotation of the first gear moves the first rod holder relative to the second rod holder to bend the implant,
    wherein the first rod holder or the second rod holder is a single, monolithic component, and
    wherein the first gear is rotated by a second gear in communication with the first gear such that the teeth of the second gear are enmeshed with the teeth of the first gear.

2. The instrument of claim 1, wherein, when mounted, the implant extends substantially perpendicular to the length of the chassis prior to bending.

3. The instrument of claim 1, wherein the first and second rod holders are mounted such that the implant extends across a center of the first gear when received within the first and second rod holders.

4. The instrument of claim 1, wherein the implant only contacts the instrument at the first rod holder and the second rod holder.

5. The instrument of claim 1, wherein one or more of the first rod holder or the second rod holder comprises a half-pipe having a pair of opposed arms that define a recess in which the implant is disposed.

6. The instrument of claim 5, wherein the pair of opposed arms taper inward such that a width of the recess at a free end of the arms is less than a width of the recess where the implant is disposed.

7. The instrument of claim 6, wherein the width of the recess at the free end is smaller than a diameter of the rod such that the implant locks within the recess by snap-fit.

8. The instrument of claim 7, wherein the first rod holder or the second rod holder comprises a lid or a set screw for securing the implant in the recess.

9. The instrument of claim 6, wherein the width of the recess at the free end is smaller than a diameter of the rod such that the implant locks within the recess by snap-fit.

10. The instrument of claim 9, wherein the first rod holder or the second rod holder comprises a lid or a set screw for securing the implant in the recess.

11. The instrument of claim 1, wherein each of the first rod holder and the second rod holder is a single, monolithic component.

12. The instrument of claim 1, wherein the second rod holder is integrally attached to the chassis.

13. The instrument of claim 1, wherein the first rod holder or the second rod holder further comprises a top portion and a base portion, with the top portion being configured to pivot relative to the base portion.

14. The instrument of claim 13, wherein rotation of the first gear moves the first rod holder to a position that is at an oblique angle with respect to the second rod holder to bend the implant, and the top portion of the first rod holder pivots with respect to the base portion to further bend the implant.

15. The instrument of claim 1, wherein the first gear is one or more of a worm gear or a conical gear.

16. The instrument of claim 1, wherein the first gear includes one or more indicia thereon for displaying a degree to which the implant is bent.

17. The instrument of claim 1, wherein the chassis further comprises a drive shaft disposed therein being configured to rotate the first gear.

18. An instrument for bending an implant, comprising:
    a chassis extending from a proximal end to a distal end to define a length therebetween;
    a gear rotatably mounted to the chassis;
    a first rod holder mounted onto the gear and configured to receive a first portion of the implant therein; and
    a second rod holder mounted onto the chassis and laterally offset from the gear in a plane defined by a diameter of the gear such that the second rod holder is disposed beyond an exterior circumferential surface of the gear, the second rod holder being configured to receive a second portion of the implant therein,
    wherein the rotation of the gear moves the first rod holder relative to the second rod holder to bend the implant, and
    wherein the bend occurs at a location along the implant that is disposed between the first rod holder and the second rod holder.

19. The instrument of claim 18, wherein the first rod holder or the second rod holder is a single, monolithic component.

20. A method of bending an implant, comprising:
    positioning the implant in an instrument having a chassis, a gear, and first and second rod holders; and
    rotating the gear to cause the first rod holder to move relative to the second rod holder to form a bend in the implant, wherein the implant only contacts the instrument at the first rod holder and the second rod holder.

21. The method of claim 20, wherein positioning the implant in the instrument further comprises mounting the implant such that a length thereof is substantially perpendicular to a length of the chassis.

22. The method of claim 20, wherein rotating the gear causes the first rod holder to pivot relative to the gear as the implant is bent.

23. The method of claim 22, wherein the pivot further comprises rotating a top portion of the first rod holder relative to a base portion thereof to further bend the implant.

24. The method of claim 20, further comprising aligning the first rod holder with the second rod holder such that an axis between a pair of arms of the first rod holder is substantially aligned with an axis between a pair of arms of the second rod holder prior to positioning the implant in the instrument.

25. An instrument for bending an implant, comprising:
a chassis extending from a proximal end to a distal end to define a length therebetween;
a gear rotatably mounted to the chassis;
a first rod holder mounted onto the gear and configured to receive a first portion of the implant therein; and
a second rod holder mounted onto the chassis and configured to receive a second portion of the implant therein,
wherein the rotation of the gear moves the first rod holder relative to the second rod holder to bend the implant,
wherein the first rod holder or the second rod holder is a single, monolithic component, and
wherein the implant only contacts the instrument at the first rod holder and the second rod holder.

26. An instrument for bending an implant, comprising:
a chassis extending from a proximal end to a distal end to define a length therebetween;
a gear rotatably mounted to the chassis;
a first rod holder mounted onto the gear and configured to receive a first portion of the implant therein; and
a second rod holder mounted onto the chassis and configured to receive a second portion of the implant therein,
wherein the rotation of the gear moves the first rod holder relative to the second rod holder to bend the implant,
wherein the first rod holder or the second rod holder is a single, monolithic component and,
wherein one or more of the first rod holder or the second rod holder comprises a half-pipe having a pair of opposed arms that define a recess in which the implant is disposed.

27. The instrument of claim 26, wherein the pair of opposed arms taper inward such that a width of the recess at a free end of the arms is less than a width of the recess where the implant is disposed.

28. An instrument for bending an implant, comprising:
a chassis extending from a proximal end to a distal end to define a length therebetween;
a gear rotatably mounted to the chassis;
a first rod holder mounted onto the gear and configured to receive a first portion of the implant therein; and
a second rod holder mounted onto the chassis and configured to receive a second portion of the implant therein,
wherein the rotation of the gear moves the first rod holder relative to the second rod holder to bend the implant, and
wherein the first rod holder or the second rod holder is a single, monolithic component, and
wherein the first rod holder or the second rod holder further comprises a top portion and a base portion, with the top portion being configured to pivot relative to the base portion.

29. The instrument of claim 28, wherein rotation of the gear moves the first rod holder to a position that is at an oblique angle with respect to the second rod holder to bend the implant, and the top portion of the first rod holder pivots with respect to the base portion to further bend the implant.

30. An instrument for bending an implant, comprising:
a chassis extending from a proximal end to a distal end to define a length therebetween;
a gear rotatably mounted to the chassis;
a first rod holder mounted onto the gear and configured to receive a first portion of the implant therein; and
a second rod holder mounted onto the chassis and configured to receive a second portion of the implant therein,
wherein the rotation of the gear moves the first rod holder relative to the second rod holder to bend the implant,
wherein the first rod holder or the second rod holder is a single, monolithic component, and
wherein the gear is one or more of a worm gear or a conical gear.

31. An instrument for bending an implant, comprising:
a chassis extending from a proximal end to a distal end to define a length therebetween;
a gear rotatably mounted to the chassis;
a first rod holder mounted onto the gear and configured to receive a first portion of the implant therein; and
a second rod holder mounted onto the chassis and configured to receive a second portion of the implant therein,
wherein the rotation of the gear moves the first rod holder relative to the second rod holder to bend the implant,
wherein the first rod holder or the second rod holder is a single, monolithic component, and
wherein the chassis further comprises a drive shaft disposed therein being configured to rotate the gear.

* * * * *